United States Patent
Edens et al.

(10) Patent No.: US 7,879,796 B2
(45) Date of Patent: Feb. 1, 2011

(54) AMINO ACID COMPOSITION FOR IMPROVING GLUCOSE TOLERANCE

(75) Inventors: Neile Edens, Columbus, OH (US); Marti S. Bergana, Blacklick, OH (US); Kati Shearer, Gahanna, OH (US); Terrence B. Mazer, New Albany, OH (US); Joseph E. Walton, Westerville, OH (US); David R. Wolf, Columbus, OH (US)

(73) Assignee: Abbott Laboratories, Abbott Park, IL (US)

( * ) Notice: Subject to any disclaimer, the term of this patent is extended or adjusted under 35 U.S.C. 154(b) by 607 days.

(21) Appl. No.: 11/385,302

(22) Filed: Mar. 21, 2006

(65) Prior Publication Data

US 2007/0225348 A1    Sep. 27, 2007

Related U.S. Application Data

(60) Provisional application No. 60/663,642, filed on Mar. 21, 2005.

(51) Int. Cl.
*A61K 38/00* (2006.01)

(52) U.S. Cl. .......................................... 514/2; 514/866

(58) Field of Classification Search ................. 514/400, 514/2, 558, 866, 904, 905
See application file for complete search history.

(56) References Cited

U.S. PATENT DOCUMENTS 3,950,529 A * 4/1976 Fischer et al. ............... 514/400
4,368,204 A * 1/1983 Sato et al. ................... 514/400
5,132,113 A   7/1992 Luca

FOREIGN PATENT DOCUMENTS

| JP | 60255722 | 12/1985 |
| JP | 4095026 A | 3/1992 |
| JP | 2003171271 A | 6/2003 |
| WO | WO02/069964 A1 | 9/2002 |

OTHER PUBLICATIONS

B. Braun Medical, Inc. HepatAmine (1982).*
"Effects of Glucose and Amino Acid Infusion on Glucose Turnover in Insulin-Resistant Obese and Type II Diabetic Patients," L. Tappy, et al, Metabolism, vol. 43, No. 4, Apr. 1994, pp. 428-434.
"Isoleucine, a potent plasma glucose-lowering amino acid, stimulates glucose uptake in $C_2C_{12}$ myotubes," Masako Doi, et al, Biochem Biophys Research Commun, 312: 1111-1117, 2003.
Aquilani, "Oral Amino Acid Administration in Patients with Diabetes Mellitus: Supplementation or Metabolic Therapy?," Am. J. Cardiol. 2004 vol. 93 {suppl}, p. 21A-22A.
Eizirik, et al., "Dietetic Supplementation with Branched Chain Amino Acids Attenuates the Severity of Streptozotocin-Induced Diabetes in Rats," 1988 Acta Diabetol., vol. 25, p. 117-126.
Nishitani, et al., "Pharmacological activities of branched-chain amino acids: augmentation of albumin synthesis in liver and improvement of glucose metabolism in skeletal muscle," Hepatology Research, 2004 vol. 30 p. S19-S24.
Office action from European Application No. 06739315.7, dated Dec. 16, 2009.

* cited by examiner

*Primary Examiner*—Kevin Weddington
(74) *Attorney, Agent, or Firm*—William J. Winter; Sandra E. Weida

(57) ABSTRACT

Disclosed are compositions, including low-calorie beverages or liquids, comprising isoleucine, leucine, valine, cysteine, and methionine, in specified amounts, weight ratios, or both. The compositions are especially useful in treating individuals afflicted with impaired glucose tolerance or diabetes.

23 Claims, 3 Drawing Sheets

AMINO ACID COMPOSITION FOR IMPROVING GLUCOSE TOLERANCE

This application claims the benefit of U.S. Provisional Application No. 60/663,642 filed Mar. 21, 2005

FIELD OF THE INVENTION

The present invention relates to compositions comprising select amino acid blends and to methods of using the compositions in individuals afflicted with impaired glucoses tolerance or diabetes.

BACKGROUND OF THE INVENTION

Diabetes mellitus is a disorder of carbohydrate metabolism resulting from insufficient production of or reduced sensitivity to insulin. In persons who have diabetes, the normal ability of body cells to use glucose is inhibited, thereby increasing blood sugar levels. As more glucose accumulates in the blood, excess levels of sugar are excreted in the urine. Corresponding symptoms of diabetes include increased urinary volume and frequency, thirst, hunger, weight loss, and weakness.

There are two variations of diabetes. Type 1 diabetes is insulin dependent diabetes mellitus for which insulin administration is required. In a subject patient with type 1 diabetes, insulin is not secreted by the pancreas and therefore must be taken by injection or inhalation. Type 2 diabetes may be controlled by dietary restriction, oral antihyperglycemic agents, and/or insulin administration. Type 2 diabetes can be attributable to dilatory pancreatic secretion of insulin and reduced sensitivity to the action of insulin on target tissues.

Complications from diabetes often involve the cardiovascular system, which then accounts for the majority of diabetes-related deaths. Other serious complications include diabetic retinopathy, kidney disease, peripheral neuropathy, and/or frequent infection.

Treatment of individuals afflicted with diabetes who are unable to produce insulin in their bodies involves the administration of regular injection or inhalation of insulin. Insulin derived from the pancreatic extract of pigs, sheep, and oxen can be used for this purpose, although many individuals now use synthetic human insulin manufactured via recombinant DNA technology.

One method of treating diabetes involves regulating or limiting calorie and carbohydrate intake by placing an individual afflicted with diabetes on a restrictive diet designed to facilitate reaching and maintaining normal body weight. While effective in theory, limiting calorie and carbohydrate intake is often difficult, thus often resulting in poor patient compliance.

Medications are also used in certain diabetic individuals to help maintain blood glucose levels within acceptable target ranges. These medications most typically stimulate insulin release by the pancreas, improve the body's ability to use insulin, and/or decrease the production of glucose by the liver. These medications, however, are limited in that each can have limiting side effects, none are appropriate for non-diabetic individuals, and the various medications often lose their effectiveness in many individuals after prolonged use.

SUMMARY OF THE INVENTION

The present invention is directed to compositions and to methods of using those compositions in treating individuals afflicted with impaired glucose tolerance or diabetes. This invention is based upon the discovery that the administration of certain amino acid combinations, in defined amounts and/or weight ratios, result in a surprisingly blunted glycemic response to a carbohydrate load.

One aspect of the present invention includes compositions comprising isoleucine, leucine, valine, cysteine, and methionine, in weight ratios of isoleucine to leucine, isoleucine to valine, isoleucine to cysteine, and isoleucine to methionine, independently of at least about 10:1.

Another aspect of the present invention includes compositions for use in treating individuals afflicted with impaired glucose tolerance or diabetes, wherein such compositions comprise from about 1 to about 200 mg/kg of body weight of isoleucine; from about 0.001 to about 10 mg/kg of body weight of leucine; from about 0.001 to about 10 mg/kg of body weight of valine; from about 0.001 to about 10 mg/kg of body weight of cysteine; and from about 0.001 to about 10 mg/kg of body weight of methionine, and wherein the weight ratios of isoleucine to leucine, isoleucine to valine, isoleucine to cysteine, and isoleucine to methionine are each independently at least about 10:1.

Another aspect of the present invention includes compositions for use in treating individuals afflicted with impaired glucose tolerance or diabetes, wherein such compositions comprise from about 10 to about 200 mg/kg of body weight of isoleucine; from about 0.01 to about 10 mg/kg of body weight of leucine; from about 0.01 to about 10 mg/kg of body weight of valine; from about 0.01 to about 10 mg/kg of body weight of cysteine; and from about 0.01 to about 10 mg/kg of body weight of methionine.

Another aspect of the present invention includes low-calorie beverages or other liquids comprising (A) about 2% to about 98% carbohydrate, as a percentage of total calories, including at least one of maltitol, erythritol, sorbitol, xylitol, mannitol, glycerol, isolmalt, and lactitol, and (B) from about 2% to about 98% of a protein source including any amino acid blend as described herein, such as those comprising isoleucine, leucine, valine, cysteine, and methionine, at weight ratios of isoleucine to leucine, isoleucine to valine, isoleucine to cysteine, and isoleucine to methionine independently of at least about 10:1. These beverages or liquids have improved flavor and are especially useful in treating individuals afflicted with impaired glucose tolerance or diabetes Another aspect of the present invention is directed to a method of treating individuals afflicted with impaired glucose tolerance or diabetes, wherein the method comprises administering to such individuals an effective amount of the compositions described herein.

DETAILED DESCRIPTION OF THE INVENTION

Figure 1:
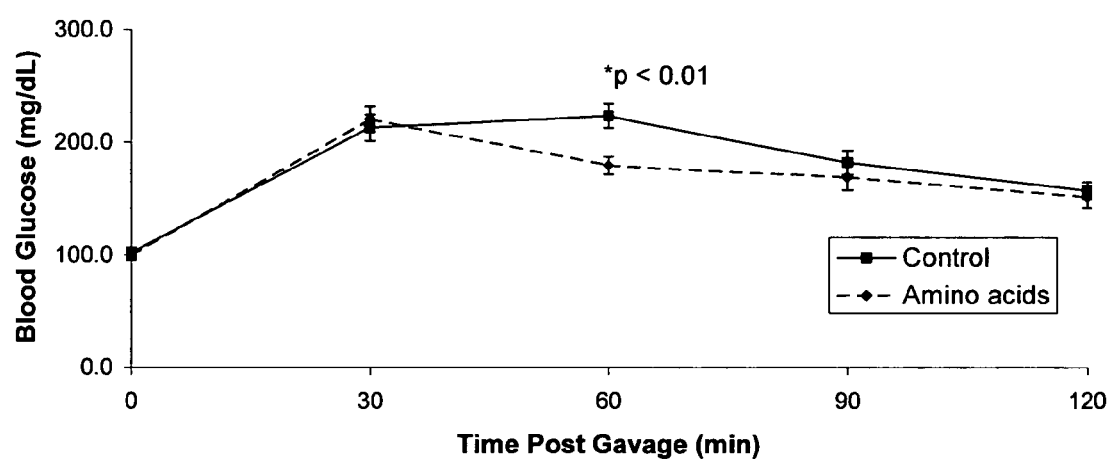
FIG. 1 is a graph illustrating changes in blood glucose concentrations over time in Fatty Zucker rats (model with impaired glucose tolerance) after oral administration of a control (glucose) solution or an amino acid test solution (with glucose) according to one aspect of the present invention.

The compositions and corresponding methods of the present invention are directed to compositions containing select blends of branched chain amino acids and sulfur-containing amino acids. These and other essential or optional elements or limitations of the compositions and methods of the present invention are described in detail hereinafter.

The compositions and methods of the present invention may comprise, consist of, or consist essentially of the essential elements and limitations of the invention described herein, as well as any additional or optional ingredients, components, or limitations described herein or otherwise useful in a nutritional or pharmaceutical application.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

All numerical ranges as used herein, whether or not expressly preceded by the term "about", are intended and understood to be preceded by that term, unless otherwise specified.

All references to singular characteristics or limitations of the present invention shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The compositions and methods of the present invention may also be substantially free of any optional ingredients described herein. In this context, the term "substantially free" means that the selected composition contains less than a functional amount of the optional ingredient, including zero percent by weight of such optional ingredient.

Product Form

The compositions of the present invention may be formulated in any known or otherwise suitable product form for oral or parenteral administration. Oral product forms are preferred and include any solid, liquid, or powder formulation suitable for use herein, provided that such a formulation allows for safe and effective oral delivery of the essential and other selected ingredients from the selected product form.

Non-limiting examples of solid nutritional product forms suitable for use herein include snack and meal replacement products, including those formulated as bars, sticks, cookies or breads or cakes or other baked goods, frozen liquids, candy, breakfast cereals, powders or granulated solids or other particulates, snack chips or bites, frozen or retorted entrees and so forth.

Non-limiting examples of liquid product forms suitable for use herein include snack and meal replacement products, hot or cold beverages, carbonated or non carbonated beverages, juices or other acidified beverages, milk or soy-based beverages, shakes, coffees, teas, enteral feeding compositions, and so forth. These liquid compositions are most typically formulated as suspensions or emulsions, but can also be formulated in any other suitable form such as solutions, liquid gels, and so forth.

Other non-limiting examples of suitable oral product forms include semi-solid or semi-liquid compositions (e.g., puddings, gels), as well as more conventional product forms such as capsules, tablets, caplets, pills, and so forth. The quantity of the composition for providing an effective amount of the defined amino acid blend to the targeted user may be contained in one or a plurality of individual dosage forms, e.g., in one tablet or a plurality of tablets.

For product forms such as lozenges, tablets (e.g. chewable, coated, etc.) pastes, or gels, the amino acid blend may be formulated at concentrations most typically ranging from about 5 to about 50%, including from about 15 to about 33%, and also including from about 15 to about 25%, by weight of the product form, all in combination with excipients or other ingredients such as carbohydrates, acidulants, flavors, and colors. The carbohydrate in these product forms preferably contains a non-reducing sugar, concentrations of which may range from about 5 to 100% by weight of the carbohydrate. Non-limiting examples of acidulants in these embodiments include citric acid, malic acid, tartaric acid, lactic acid, or combinations thereof, to enhance salivation and to provide taste masking for the amino acid bitter or brothy notes.

Amino Acid Blend

The compositions of the present invention comprise a select blend of branched chain amino acids and sulfur-containing amino acids, the former of which includes valine (VAL), leucine (LEU), and isoleucine (ILE), and the latter of which includes cysteine (CYS) and methionine (MET).

The compositions of the present invention therefore includes an amino acid blend of least isoleucine, leucine, valine, cysteine, and methionine, the quantity or amount of which should be sufficient to provide an effective treatment for at least one of impaired glucose tolerance or diabetes.

In one embodiment of the present invention, the composition contains from about 1.0 to about 200 mg/kg of body weight of isoleucine; from about 0.001 to about 10 mg/kg of body weight of leucine; from about 0.001 to about 10 mg/kg of body weight of valine; from about 0.001 to about 10 mg/kg of body weight of cysteine; and from about 0.001 to about 10 mg/kg of body weight of methionine. Body weight refers to body weight of the subject or subject patient to which the composition is administered.

In another embodiment of the present invention, the composition contains from about 120 to about 180 mg/kg of body weight of isoleucine; from about 0.25 to about 7.5 mg/kg of body weight of leucine; from about 0.25 to about 7.5 mg/kg of body weight of valine; from about 0.25 to about 7.5 mg/kg of body weight of cysteine; and from about 0.2 to about 5 mg/kg of body weight of methionine.

In another embodiment of the present invention, the composition contains from about 130 to about 170 mg/kg of body weight of isoleucine; from about 0.5 to about 5 mg/kg of body weight of leucine; from about 0.5 to about 5 mg/kg of body weight of valine; from about 0.5 to about 5 mg/kg of body weight of cysteine; and from about 0.3 to about 3 mg/kg of body weight of methionine.

The amount of amino acids for use in the select blends may also be characterized as a weight ratio of the branched chain to sulfur-containing amino acids of at least about 10:1, including at least about 50:1, and also including at least about 100:1, and also including from 500:1 to 10:1.

The amount of amino acids for use in the selected blends may also be characterized by other defined weight ratios of amino acids that ultimately contribute to the efficacy of treating at least one of impaired glucose tolerance or diabetes.

In one such embodiment of the present invention, the composition has weight ratios of isoleucine to leucine, isoleucine to valine, isoleucine to cysteine, and isoleucine to methionine independently of at least about 10:1.

In another embodiment, the weight ratio of at least one (such as at least two of, at least three of, at least four of, and all of) of isoleucine to leucine, isoleucine to valine, isoleucine to cysteine, and isoleucine to methionine, is at least about 50:1, including at least about 100:1 and also including from about 50:1 to about 500:1.

The individual amino acids for use in the compositions and methods of the present invention can be derived from or provided by any known or otherwise conventional amino acid source, including amino acids esters or acylated derivatives, amino acids salified with inorganic or organic bases. The esterified forms are often derived from straight or branched chain alcohols, whereas the salified forms often include hydrochlorides, sulfates, acetates, glutamates, and so forth.

The individual amino acids used in the amino acid blends of the present invention include chemically discrete amino acids unattached to any protein or other polypeptide structure. Although less preferred, the amino acids can also be provided by a synthetic polypeptide that provides the requisite amount and/or weight ratios of the amino acids in the defined blend. Although the compositions may further comprise natural or intact proteins, or even polypeptide fragments thereof, the amino acids in such proteins or segments are not considered in the determination of the requisite amino acid selection, including amounts and/or weight ratios, in the amino acid blend as defined herein.

The amino acids in the defined blend may be in the L or R configuration, or a mixture thereof, although most amino acids for use in the formulation will typically be in the L configuration. The amino acids used herein are commercially available from a number of different material suppliers, including Sigma-Aldrich Corporation, having a place of business at 3050 Spruce Street, St. Louis, Mo.

When a composition of the present invention is in liquid form, most typically as an oral liquid or beverage, or after a powder embodiment is reconstituted to form an oral liquid composition, the pH of the liquid composition is suitable for appropriate administration to a subject, such as by oral administration. In one such liquid embodiment, the composition has a pH from about 2.5 to about 8.0, including from about 2.7 to about 7.0, and also including from about 3.0 to about 5.5, and also including from about 3.0 to about 5.0.

The compositions of the present invention may further comprise one or more supplemental amino acids, non-limiting examples of which include aspartic acid (ASP), threonine (THR), serine (SER), glutamic acid (GLU), proline (PRO), glycine (GLY), alanine (ALA), tyrosine (TYR), histidine (HIS), lysine (LYS), arginine (ARG), methionine (MET), tryptophan (TRY), phenylalanine (PHE), and combinations thereof. The compositions may contain a sufficient amount of one or more (such as at least about 2 or more, and at least about 5 or more) supplemental amino acids to contribute to providing a treatment for at least one of impaired glucose tolerance and diabetes.

In one embodiment of the present invention, the composition contains one or more of from about 0.01 to about 30 mg/kg (including from about 1 to about 30 mg/kg and also including from about 5 to about 20 mg/kg) of body weight of each of aspartic acid and glutamic acid; from about 0.001 to about 10 mg/kg (including from about 0.1 to about 10 mg/kg and also including from about 0.5 to about 5 mg/kg) of body weight of each of threonine, serine, proline, histidine, and lysine; and from about 0.001 to about 20 mg/kg (including from about 0.1 to about 20 mg/kg and also including from about 1 to about 10 mg/kg) of body weight of each of glycine, alanine, tyrosine, arginine, and tryptophan.

In some instances, the compositions of the present invention contain little or no phenylalanine. For example, the composition may contain less than about 10 mg/kg of body weight of phenylalanine or less than about 5% by weight. In another embodiment, the composition contains less than about 5 mg/kg of body weight of phenylalanine. In yet another embodiment, the composition contains zero or less than about 1 mg/kg of body weight of phenylalanine.

Macronutrients

The compositions of the present invention may further comprise one or more other macronutrients including a fat source, a carbohydrate source, and a protein source, all in addition to the amino acids blend as defined herein.

The optional macronutrients in combination with the other essential or added ingredients may provide up to about 1000 kcal of energy per serving or dose, including from about 25 kcal to about 900 kcal, also including from about 75 kcal to about 700 kcal, also including from about 100 kcal to about 500 kcal, also including from about 150 kcal to about 400 kcal, and also including from about 200 kcal to about 300 kcal, per serving or dose, preferably as a single, undivided serving or dose.

Many different sources and types of proteins, lipids, and carbohydrates are known and can be used in the various products described herein, provided that the selected nutrients are safe and effective for oral administration and are compatible with the essential and other added ingredients.

Carbohydrates suitable for use in the compositions of the present invention may be simple, complex, or variations or combinations thereof. Non-limiting examples of suitable carbohydrates include hydrolyzed or modified starch or cornstarch, maltodextrin, glucose polymers, sucrose, corn syrup, corn syrup solids, rice-derived carbohydrate, glucose, fructose, lactose, high fructose corn syrup, indigestible oligosaccharides (e.g., fructooligosaccharides), soluble or insoluble fiber, honey, sugar alcohols (e.g., maltitol, erythritol, sorbitol), and combinations thereof.

Proteins suitable for use in the compositions of the present invention, in addition to the amino acid blend component as described herein, include hydrolyzed, partially hydrolyzed or non-hydrolyzed proteins or protein sources, and can be derived from any known or otherwise suitable source such as milk (e.g., casein, whey), animal (e.g., meat, fish), cereal (e.g., rice, corn), vegetable (e.g., soy), or combinations thereof.

Fats suitable for use in the compositions of the present invention include coconut oil, fractionated coconut oil, soy oil, corn oil, olive oil, safflower oil, high oleic safflower oil, MCT oil (medium chain triglycerides), sunflower oil, high oleic sunflower oil, palm and palm kernel oils, palm olein, canola oil, marine oils, cottonseed oils, and combinations thereof.

The concentration or amount of fat, protein, and carbohydrate in the compositions of the present invention may vary considerably depending upon the particular product form (e.g., solid, liquid, powder) and the various other formulations and targeted dietary needs. These macronutrients are most typically formulated within any of the caloric ranges (embodiments A-D) described in the following table.

|  | Nutritional Embodiments* | | | |
| --- | --- | --- | --- | --- |
| Nutrients | A | B | C | D |
| Carbohydrate % total calories | 0-98 | 2-96 | 10-75 | 30-50 |
| Fat % total calories | 0-98 | 2-96 | 20-85 | 35-55 |
| Protein % total calories | 0-98 | 2-96 | 5-70 | 15-35 |

*Each numerical value is preceded by the term "about"

Other Optional Ingredients

The compositions of the present invention may further comprise other optional components that may modify the physical, chemical, aesthetic or processing characteristics of the products or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the essential and other ingredients in the selected product form.

Non-limiting examples of such optional ingredients include preservatives, anti-oxidants, emulsifying agents, buffers, pharmaceutical actives, additional nutrients as described herein, colorants, flavors, thickening agents and stabilizers, emulsifying agents, lubricants, and so forth.

The compositions of the present invention may further comprise an sweetening agent, preferably including at least one sugar alcohol such as maltitol, crythritol, sorbitol, xylitol, mannitol, isolmalt, and lactitol, and also preferably including at least one artificial or high potency sweetener such as acesulfame K, aspartame, sucralose, saccharin, stevia, and tagatose. These sweetening agents, especially as a combination of a sugar alcohol and an artificial sweetener, are especially useful in formulating liquid beverage embodiments of the present invention having a desirable favor profile. These sweetener combinations are especially effective in masking undesirable flavors sometimes associated with the addition of amino acids to a liquid beverage. Optional sugar alcohol concentrations in the beverage may range from at least about 0.01%, including from 0.1% to about 10%, and also including from about 1% to about 6%, by weight of the beverage. Optional artificial sweetener concentrations may range from about 0.01%, including from about 0.05% to about 5%, also including from about 0.1% to about 1.0%, by weight of the beverage.

The compositions of the present invention may further comprise any of a variety of other vitamins or related nutrients, non-limiting examples of which include vitamin A, vitamin D, vitamin E, vitamin K, thiamine, riboflavin, pyridoxine, vitamin $B_{12}$, carotenoids (e.g., beta-carotene, zeaxanthin, lutein, lycopene), niacin, folic acid, pantothenic acid, biotin, vitamin C, choline, inositol, salts and derivatives thereof, and combinations thereof.

The compositions may further comprise any of a variety of other additional minerals, non-limiting examples of which include calcium, phosphorus, magnesium, iron, zinc, manganese, copper, sodium, potassium, molybdenum, chromium, chloride, and combinations thereof.

Low-Calorie Beverage or Liquid

The compositions of the present invention include low-calorie beverages or other liquids formulated to mask or otherwise minimize undesirable flavor associated with the amino acid blends described herein.

These low calorie beverages or liquids include those embodiments comprising from about 2% to about 98% of a protein source, as a percentage of total calories, including any of the amino acid blends as described herein, such as those comprising isoleucine, leucine, valine, cysteine, and methionine, at weight ratios of isoleucine to leucine, isoleucine to valine, isoleucine to cysteine, and isoleucine to methionine independently of at least about 10:1; and from about 2% to about 98% carbohydrate, as a percentage of total calories, including at least one of maltitol, erythritol, sorbitol, xylitol, mannitol, glycerol, isolmalt, and lactitol; wherein the nutritional liquid has a pH of from about 2.5 to about 8.0, preferably from about 2.5 to 4.6, and a caloric density of from about 8.1 kcal/100 ml to about 40 kcal/100 ml, including from about 16 kcal/100 ml to about 32 kcal/100 ml.

These low calorie beverages or liquids preferably include erythritol, concentrations of which may range from about 0.1 to about 10%, including from about 1 to about 5%, and also including from about 1.5 to about 3%, all by weight of the beverage or liquid.

These low calorie beverages or liquids preferably include at least one additional sweetening agent, some non-limiting examples of which include acesulfame K, aspartame, sucralose, saccharin, stevia, and tagatose.

These low calorie beverages or liquids may further comprise any one or more of the other optional or other ingredients as described herein.

Manufacture

The compositions of the present invention may be prepared by any known or otherwise effective manufacturing technique for preparing the selected product form. Many such techniques are known for any given product form such as nutritional liquids or nutritional bars and can easily be applied by one of ordinary skill in the art to the nutritional products described herein.

The compositions of the present invention can likewise be prepared by any known or otherwise effective manufacturing technique for preparing the various pharmaceutical product forms. Many such techniques are known for any given pharmaceutical product form such as capsules, tablets, liquids, and so forth, and can easily be applied by one of ordinary skill in the art to the compositions described herein.

As a basic liquid formulation, the compositions of the present invention may be prepared by dissolving each of the selected amino acids in water or a dilute acid solution, and then combining the different amino acid solutions to form a liquid embodiment of the present invention.

As a basic solid formulation, the compositions of the present invention may be prepared by combining the different powder forms of the selected amino acids, along with any tablet forming materials or other excipients, and then dry blending the powders prior to processing it into the desired solid product form, e.g., tablet, capsule, caplet, and so forth.

In yet another embodiment, the compositions of the present invention may be formulated as a nutritional liquid, including a juice or milk or soy-based liquid, comprising the selected amino acid blend. Such an embodiment may be prepared by first forming an oil and fiber blend containing all formulation oils, any emulsifier, fiber and fat-soluble vitamins. Additional slurries (typically a carbohydrate and two protein slurries) are prepared separately by mixing the carbohydrate and minerals together and the protein in water. The slurries are then mixed together with the oil blend. The resulting mixture is homogenized, heat processed, standardized with any water-soluble vitamins, flavored and the liquid terminally sterilized or aseptically filled or dried to produce a powder.

Other product forms such nutritional bars may be manufactured, for example, using cold extrusion technology as is known and commonly described in the bar manufacturing art. To prepare such compositions, typically all of the powdered components are dry blended together, which typically includes the amino acid blend and any proteins, vitamin premixes, certain carbohydrates, and so forth. The fat-soluble components are then blended together and mixed with any powdered premixes. Finally any liquid components are then mixed into the composition, forming a plastic like composition or dough. The resulting plastic mass can then be shaped, without further physical or chemical changes occurring, by cold forming or extrusion, wherein the plastic mass is forced at relatively low pressure through a die, which confers the desired shape. The resultant exudate is then cut off at an appropriate position to give products of the desired weight. If desired the solid product is then coated, to enhance palatability, and packaged for distribution.

The solid nutritional embodiments of the present invention may also be manufactured through a baked application or heated extrusion to produce solid product forms such as cereals, cookies, crackers, and similar other product forms. One knowledgeable in the nutrition manufacturing arts is able to select one of the many known or otherwise available manufacturing processes to produce the desired final product.

The compositions of the present invention may, of course, be manufactured by other known or otherwise suitable techniques not specifically described herein without departing from the spirit and scope of the present invention. The present embodiments are, therefore, to be considered in all respects as illustrative and not restrictive and that all changes and equivalents also come within the description of the present invention. The following non-limiting examples will further illustrate the compositions and methods of the present invention.

Method of Use

The compositions of the present invention may be used in individuals afflicted with or otherwise at risk of developing impaired glucose tolerance or diabetes. These compositions can also be administered, however, in any individual as a nutrition source, especially in those in whom a blunted glycemic response is desirable.

The compositions and methods of the present invention may be directed to any individual, including humans and other mammals such dogs, cats, rodents, cows, sheep, swine, goats, horses and other hoofed animals, and so forth. Healthy individuals at risk of type 2 diabetes may be administered the compositions as well.

The compositions of the present invention may be administered before, during, or after carbohydrate intake (such as from a meal, drink, or snack) to improve glucose tolerance and reduce the glycemic response. In one embodiment, the administration of the amino acid composition is conducted within about one hour of carbohydrate consumption by the subject. In another embodiment, the administration of the amino acid composition is conducted within about 30 minutes of carbohydrate consumption by the subject.

The compositions of the subject invention may be used to treat glucose tolerance, diabetes, obesity, and/or symptoms and side effects of glucose tolerance, diabetes, and obesity. Specifically, the compositions may be used to treat type 2 diabetes, type 2 diabetes and/or symptoms of any thereof. Symptoms and side effects of diabetes include one or more of high blood glucose levels, sleep habits such as insomnia, general energy level such as lethargy, strength, body weight/poor or increased appetite, reflux, irregularity, stomach neuropathy, kidney failure, heart disease, stroke, and deteriorating eyesight.

In one aspect of the invention, administration of the compositions of the subject invention to a subject in need thereof after, during, or before carbohydrate ingestion decreases blood glucose levels compared to carbohydrate ingestion without the administration of the compositions of the subject invention. Blood glucose levels may be determined using whole blood, blood plasma or blood serum. Unless otherwise indicated, blood glucose levels refer to analysis of whole blood. Administration of the amino acid compositions decreases blood glucose levels after carbohydrate ingestion (compared to blood glucose levels after carbohydrate ingestion without administration of the amino acid compositions) in at least one of about 30 minutes after carbohydrate intake, about 60 minutes after carbohydrate intake, about 90 minutes after carbohydrate intake, and about 120 minutes after carbohydrate intake.

In another aspect of the invention, administration of the compositions of the present invention to an individual before, during, or after carbohydrate intake decreases blood glucose levels compared to the same carbohydrate intake without the administration of the compositions of the present invention by at least about 5% in at least one of about 30 minutes after carbohydrate intake, about 60 minutes after carbohydrate intake, about 90 minutes after carbohydrate intake, and about 120 minutes after carbohydrate intake.

In yet another aspect of the invention, administration of the compositions of the present invention to a subject before, during, or after carbohydrate intake decreases blood glucose level compared to the same carbohydrate intake without the administration of the compositions of the subject invention by at least about 10% in at least one of about 30 minutes after carbohydrate intake, about 60 minutes after carbohydrate intake, about 90 minutes after carbohydrate intake, and about 120 minutes after carbohydrate intake.

In still yet another aspect of the invention, administration of the compositions of the subject invention to a subject before, during, or after carbohydrate intake decreases blood glucose levels compared to the same carbohydrate intake without the administration of the compositions of the subject invention by at least about 20% in at least one of about 30 minutes after carbohydrate intake, about 60 minutes after carbohydrate intake, about 90 minutes after carbohydrate intake, and about 120 minutes after carbohydrate intake.

EXAMPLES

The following examples illustrate specific embodiments of the compositions and methods of the present invention, including some suitable techniques to prepare the compositions. The examples are given solely for the purpose of illustration and are not to be construed as limitations of the present invention, as many variations thereof are possible without departing from the spirit and scope of the invention.

Examples 1-3

Examples 1-3 illustrate nutritional liquid embodiments of the present invention. Also included are corresponding methods of using the compositions in accordance with the methods of the present invention. The ingredients for each exemplified composition are described in the following table. All ingredient amounts are listed as kg per 1000 kg batch of product, unless otherwise specified.

| Ingredient | | Low-calorie Beverage* | | |
|---|---|---|---|---|
| | | Example 1 (kg) | Example 2 (kg) | Example 3 (kg) |
| Water | | 412.4 | 412.4 | 412.4 |
| Phosphoric acid 80% | | 27.49 | 27.49 | 27.49 |
| 45% KOH | | 8.247 | 8.247 | 8.247 |
| Citric acid | | 0.2749 | 0.2749 | 0.2749 |
| Eridex ™ (Erythritol) | | 23.37 | 23.37 | 23.37 |
| Maltitol powder | | 12.37 | 12.37 | 12.37 |
| Acesulfame K (10%) solution | | 0.5910 | 0.5910 | 0.5910 |
| Sucralose liquid (25%) solution | | 0.5910 | 0.5910 | 0.5910 |
| Amino Acid Blend | Isoleucine | 16.62 | 8.31 | 33.24 |
| | Cystine 2 HCL | 0.3111 | 0.156 | 0.622 |
| | Methionine | 0.05910 | 0.03 | 0.118 |
| | Valine | 0.1182 | 0.059 | 0.236 |
| | Leucine | 0.1155 | 0.058 | 0.231 |
| | (Total) | (17.22) | 8.614 | 34.447 |
| Flavor Blend | Meringue | 0.6873 | 0.6873 | 0.6873 |
| | National Lime | 0.5154 | 0.5154 | 0.5154 |
| | Lemon | 0.5154 | 0.5154 | 0.5154 |
| | (Total) | (1.718) | (1.718) | (1.718) |

*Total calories: 72.432 kcal/11 oz (23 kcal/100 ml)

Each of the exemplified embodiments of the present invention as referenced in the preceding table may be prepared, for example, in accordance with the following batching and processing instructions.

The amino acid blend is prepared by conventional methods as a powder comprising each of the identified amino acids. The amino acid powder is added slowly, with agitation, to a kettle containing the specified amount of water. Once the amino acids are fully dispersed, the solution pH is reduced to 2.4 using an 80% phosphoric acid solution, and thereafter increased to 3.2 using a 45% KOH solution.

To the pH-adjusted blend, the specified amounts of the premix flavor blend, citric acid, erythritol, powdered maltitol, 10% Acesulfame potassium solution, and liquid sucralose, are added and allowed to mix thoroughly. The resulting mixture is then subjected to minimal homogenization pressure, UHT (ultra high temperature) processing at 104° C. for 5 seconds, and then hot aseptic filling into suitable containers at a temperature of 88-99° C. The pH of the final product is approximately 3.2.

Each exemplified beverage has a weight ratios of isoleucine to leucine, isoleucine to valine, isoleucine to cysteine, and isoleucine to methionine, of at least about 10:1.

Each of the exemplified beverages is used to treat individuals afflicted with impaired glucose tolerance. Each is administered, within one hour of a carbohydrate-containing meal or other carbohydrate challenge, to such individuals to the extent necessary to provide 1-200 mg/kg of body weight of isoleucine; 0.001-10 mg/kg of body weight of leucine; 0.001-10 mg/kg of body weight of valine; 0.001-10 mg/kg of body weight of cysteine; and 0.001-10 mg/kg of body weight of methionine.

Blood glucose levels in these individuals following the carbohydrate-containing meal or other carbohydrate challenge are reduced as compared to blood glucose levels without administration of the beverage by at least 5-10% in at least one of about 30 minutes after carbohydrate intake, about 60 minutes after carbohydrate intake, about 90 minutes after carbohydrate intake, and about 120 minutes after carbohydrate intake.

Examples 4-6

Examples 4-6 illustrate some of the possible tablet embodiments of the present invention. Also included are corresponding methods of using the tablets in accordance with the methods of the present invention. The tablets are made by methods well known in the formulation arts.

| | Example 4 | | Example 5 | | Example 6 | |
|---|---|---|---|---|---|---|
| Ingredient | Gm/100 g batch | Gm/2 gm tablet | Gm/100 g batch | Gm/2 gm tablet | Gm/100 g batch | Gm/2 gm tablet |
| Amino acid blend* | 25.0 | 0.5 | 25.0 | 0.5 | 25 | 0.5 |
| Powdered sucralose | 0.133 | 0.00266 | 0.133 | 0.00266 | 0.166 | 0.00332 |
| Acesulfame K | 0.023 | 0.00046 | 0.023 | 0.00046 | 0.029 | 0.00058 |
| Meringue flavor | 1.0 | 0.02 | 1 | 0.02 | 1 | 0.02 |
| Lime flavor | 0.75 | 0.015 | 0.75 | 0.015 | 0.75 | 0.015 |
| Lemon flavor | 0.75 | 0.015 | 0.75 | 0.015 | 0.75 | 0.015 |
| Fructose | 34.673 | 0.69346 | 65.876 | 1.31752 | — | — |
| Powdered Maltitol | 12.135 | 0.2427 | 1.214 | 0.02428 | 18 | 0.36 |
| Erythritol | 22.536 | 0.45072 | 2.254 | 0.04508 | 34 | 0.68 |
| Citric Acid | 3.0 | 0.06 | 3 | 0.06 | 3 | 0.06 |
| Trehalose | — | — | — | — | 17.305 | 0.3461 |
| Total | 100 | 2 | | | | |

*Amino acid blend from Example 1

Each exemplified tablet has weight ratios of isoleucine to leucine, isoleucine to valine, isoleucine to cysteine, and isoleucine to methionine, of at least about 10:1.

Each of the exemplified tablets is used to treat individuals afflicted with impaired glucose tolerance. Each is administered, as single or multiple tablets, within one hour of a carbohydrate-containing meal or other carbohydrate challenge, to such individuals to the extent necessary to provide 1-200 mg/kg of body weight of isoleucine; 0.001-10 mg/kg of body weight of leucine; 0.001-10 mg/kg of body weight of valine; 0.001-10 mg/kg of body weight of cysteine; and 0.001-10 mg/kg of body weight of methionine. A typical dose is 25 tablets daily, taken orally in divided doses. These tablets may be swallowed whole or chewed, but are most typically chewed.

Blood glucose levels in these individuals following the carbohydrate-containing meal or other carbohydrate challenge are reduced as compared to blood glucose levels without administration of the beverage by at least 5-10% in at least one of about 30 minutes after carbohydrate intake, about 60 minutes after carbohydrate intake, about 90 minutes after carbohydrate intake, and about 120 minutes after carbohydrate intake.

Experiment

The following experiments are directed to the compositions of the present invention, and include the administration of these compositions to rats with impaired glucose tolerance (Fatty Zucker rats) or to rats with Type 2 diabetes mellitus (Zucker Diabetic Fatty rats) and the subsequent evaluation of the blood glucose response in each animal.

Experiment 1

An amino acid test formula and control are prepared. The control is a 22.5% glucose solution. The amino acid test formula is prepared by weighing and dissolving each of the following amino acids in separate tubes: ASP (66.55 mg) is dissolved in 1.0 ml of 1N HCL; THR (7.21 mg) is dissolved in 1.0 ml of water; SER (7.97 mg) is dissolved in 1.0 ml of water; GLU (102.3 mg) is dissolved in 1.0 ml of 1N HCL; PRO (8.6 mg) is dissolved in 1.0 ml of water; GLY (29.15 mg) is dissolved in 1.0 ml 1N HCL; ALA (33.27 mg) is dissolved in 1.0 ml of water; CYS (5.28 mg) is dissolved in 1.0 ml 1N HCL; VAL (6.68 mg) is dissolved in 1.0 ml of water; MET (3.36 mg) is dissolved in 1.0 ml of water; ILE (7.34 mg) is dissolved in 1.0 ml of 1N HCL; LEU (6.58 mg) is dissolved in 1.0 ml of 1N HCL; TRY (33.55 mg) is dissolved in 1.0 ml of 1N HCL; PHE (20.8 mg) is dissolved in 1.0 ml of 1N HCL; HIS (6.9 mg) is dissolved in 1.0 ml of 1N HCL; LYS (11.8 mg) is dissolved in 1.0 ml of water; ARG (34.38 mg) is dissolved in 1.0 ml of water; TRP (9.46 mg) is dissolved in 1.0 ml of 1 N HCL. Each amino acid additive is contained within in its own individual tube and is mixed within that tube until a clear solution forms.

Among the different amino acid solutions formed, those dissolved with HCL are then combined in a 50 ml beaker, after which 937.5 mg of ILE is added to the beaker and mixed until dissolved. Once the ILE is dissolved, all amino acid solutions once dissolved in water are then added to the beaker, followed by 25 ml of a 45% glucose solution. The resulting glucose-containing blend is stirred until thoroughly mixed, the pH of which is then adjusted to 7.0+/−1.0 with a 50% sodium hydroxide solution (buffer may be added to stabilize pH). The pH adjusted mixture is transferred to a 50 ml volumetric flask and brought to volume with distilled water. The mixture is transferred to a beaker with a stir bar and stirring is continued while filling syringes.

Fatty Zucker rats are received at the animal facility for at least one week before testing. Each is weighed the day before the experiment and then assigned to one of two groups matched for body weight. Only rats that weigh at least 300 gm are included in the study. After an overnight fast, each rat is weighed again and then dosed at 8 ml/kg body weight (oral gavage) with the control or the amino acid test solution. Blood glucose concentrations are then measured from the tip of the tail of each animal at 30, 60, 90 and 120 minutes following the gavage.

The data from this experiment are summarized in FIG. 1, which shows that the amino acid test mixture, when administered to the rats, significantly reduces blood glucose concentrations relative to the control at 60 minutes following gavage.

Experiment 2

The control formula (22.5% glucose solution) and the amino acid test formula described in Experiment 1 are prepared and subsequently used in this second experiment, along with an isoleucine mixture as described below.

In this second experiment, a high dose isoleucine mixture is prepared by adding L-isoleucine (1338.7 g) to 50 ml beaker followed by 10 ml of 1N HCL. The beaker contents are mixed until dissolved, and thereafter to it is added with agitation 25 ml of a 45% glucose solution. The pH of the resulting mixture is adjusted to 7.0 (+/−1.0) with a 50% sodium hydroxide solution (buffer may be added to stabilize pH). The pH adjusted mixture is transferred to a 50 ml volumetric and brought to volume with distilled water. The mixture is transferred to a beaker with stir bar and continually stirred while filling syringes.

Zucker Diabetic Fatty rats, a model of type 2 diabetes, are received at the animal facility for at least one week before testing. Each is weighed the day before the experiment and then assigned to one of two groups matched for body weight. After an overnight fast, each rat is weighed and then dosed at 8 ml/kg body weight (oral gavage) with the glucose control, the amino acid test mixture, or the isoleucine solution. Blood glucose concentrations are then measured from the tip of the tail of each animal at 30, 60, 90 and 120 minutes following the gavage.

Figure 2:
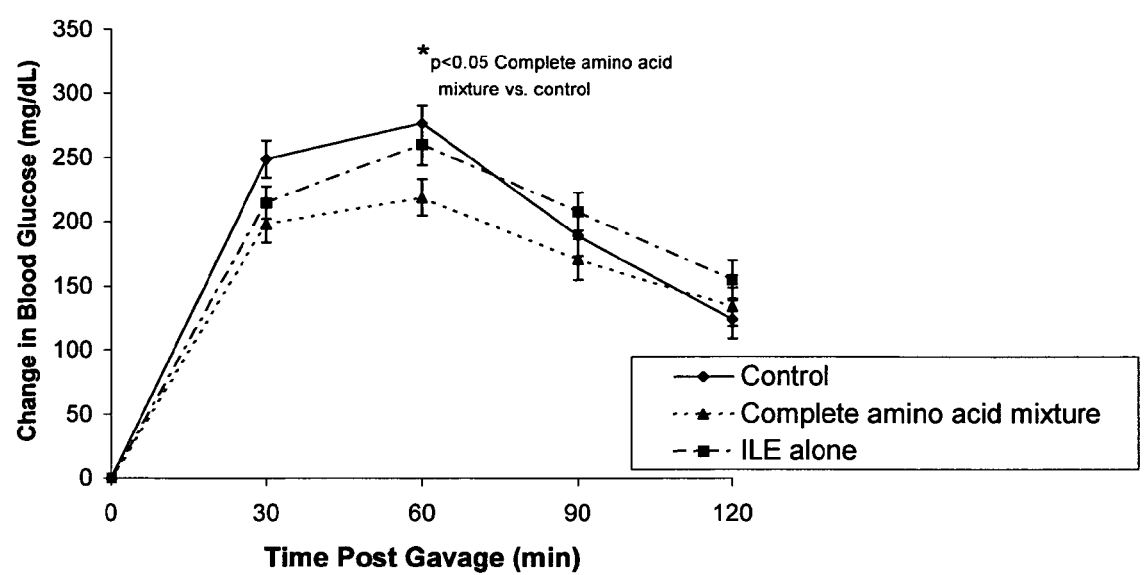
FIG. 2 is a graph illustrating changes in blood glucose concentrations over time in Zucker Diabetic Fatty rats (model with type 2 diabetes mellitus) after oral administration of a control (glucose) solution, an isoleucine solution (with glucose), or an amino acid test solution (with glucose) according to one aspect of the present invention.

The data from this experiment are summarized in FIG. 2. As shown in the illustrated data, high dose isoleucine (isoleucine alone) does not significantly affect blood glucose concentrations relative to the control, whereas the amino acid test mixture significantly decreases blood glucose concentrations relative to the control at 60 minutes following gavage.

Experiment 3

To determine the minimal amino acid solution needed to improve glycemia, an amino acid mixture is prepared in the following manner (weigh each amino acid and place it into its own individual tube): CYS (5.28 mg) is dissolved in 1.0 ml 1N HCL; VAL (6.68 mg) is dissolved in 1.0 ml of water; MET (3.36 mg) is dissolved in 1.0 ml of water; and LEU (6.58 mg) is dissolved in 1.0 ml of 1N HCL. Each tube is mixed until a clear solution is obtained. In a 50 ml beaker, ILE (927.5 mg) is dissolved in 10 ml HCL. All amino acid tubes dissolved in acid are added to the 50 ml beaker (use a pipette to transfer) and stirred. All of the amino acids once dissolved in water are then added to the beaker (transfer via pipette), followed by 25 ml of 45% glucose solution. The resulting blend is stirred until thoroughly mixed. The pH of the blend is adjusted to about 7 with a 50% sodium hydroxide solution. A buffer may be added to stabilize the pH. The blend is then transferred to a 50 ml volumetric flask and brought to volume with distilled water. The resulting mixture is compared to a control solution of 22.5% glucose in the following experiment.

Fatty Zucker rats are received at the animal facility for at least one week before testing. Each is weighed the day before the experiment, and then assigned to one of two groups matched for body weight. Only rats that weigh at least 300 gm are included in the study. After an overnight fast, the rats are weighed and dosed at 8 ml/kg body weight (oral gavage) with either control or the amino acid test mixture. Blood glucose concentrations are then measured from the tip of the tail of each animal at 30, 60, 90 and 120 minutes from the tip of the tail.

Figure 3:
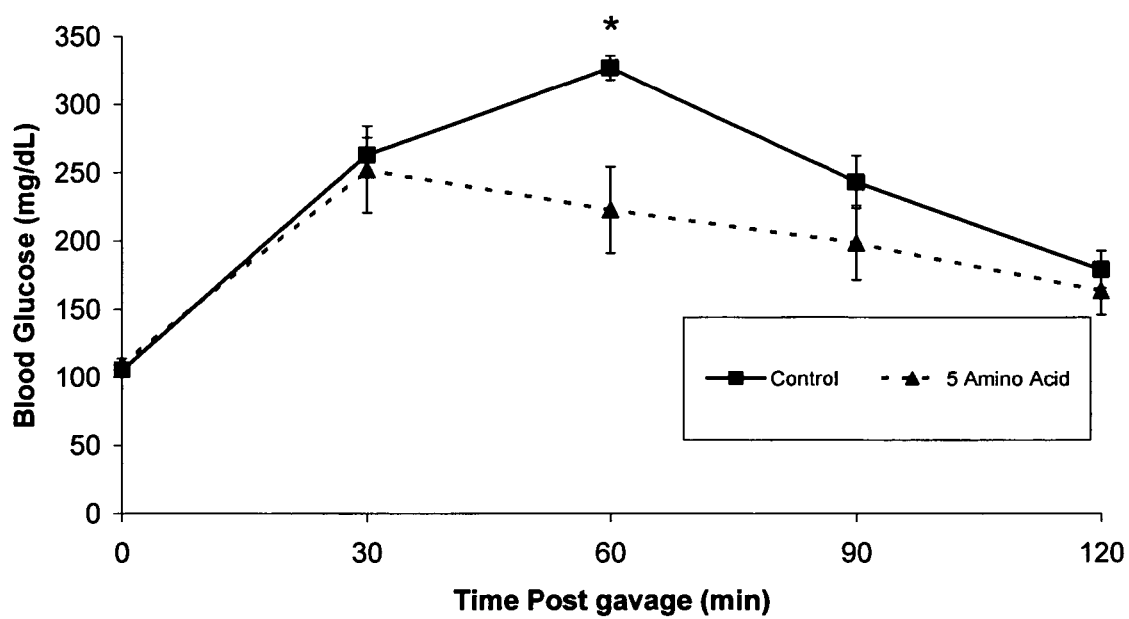
FIG. 3 is a graph illustrating changes in blood glucose concentrations over time in Fatty Zucker rats (model with impaired glucose tolerance) after oral administration of a control (glucose) solution or an amino acid test solution (with glucose) according to one aspect of the present invention.

The data from this experiment are summarized in FIG. 3, which shows that the amino acid test mixture (five amino acid combination) significantly decreases blood glucose concentration relative to the control at 60 minutes following gavage.

What is claimed is:

1. An oral composition for treating individuals afflicted with diabetes or impaired glucose tolerance, comprising:
    about 1 to about 200 mg/kg of body weight of isoleucine;
    about 0.001 to about 10 mg/kg of body weight of leucine;
    about 0.001 to about 10 mg/kg of body weight of valine;
    about 0.001 to about 10 mg/kg of body weight of cysteine; and
    about 0.001 to about 10 mg/kg of body weight of methionine,
    wherein weight ratios of isoleucine to leucine, isoleucine to valine, isoleucine to cysteine, and isoleucine to methionine are independently at least about 10:1.

2. An oral composition for treating individuals afflicted with diabetes or impaired glucose tolerance, comprising:
    about 1 to about 200 mg/kg of body weight of isoleucine;
    about 0.001 to about 10 mg/kg of body weight of leucine;
    about 0.001 to about 10 mg/kg of body weight of valine;
    about 0.001 to about 10 mg/kg of body weight of cysteine; and
    about 0.001 to about 10 mg/kg of body weight of methionine,
    wherein weight ratios of isoleucine to leucine, isoleucine to valine, isoleucine to cysteine, and isoleucine to methionine are independently at least about 10:1; and
    wherein the composition further comprises at least one of:
    about 0.01 to about 30 mg/kg of body weight of aspartic acid;
    about 0.001 to about 10 mg/kg of body weight of threonine;
    about 0.001 to about 10 mg/kg of body weight of serine;
    about 0.01 to about 30 mg/kg of body weight of glutamic acid;
    about 0.001 to about 10 mg/kg of body weight of proline;
    about 0.001 to about 20 mg/kg of body weight of glycine;
    about 0.001 to about 20 mg/kg of body weight of alanine;
    about 0.001 to about 20 mg/kg of body weight of tyrosine;
    about 0.001 to about 10 mg/kg of body weight of histidine;
    about 0.001 to about 10 mg/kg of body weight of lysine;
    about 0.001 to about 20 mg/kg of body weight of arginine; and
    about 0.001 to about 20 mg/kg of body weight of tryptophan.

3. The composition of claim 1, wherein the weight ratio of at least one of isoleucine to leucine, isoleucine to valine, isoleucine to cysteine, and isoleucine to methionine is at least about 100:1.

4. The composition of claim 1 comprising less than about 10 mg/kg of body weight of phenylalanine.

5. The composition of claim 1 further comprising at least one of vitamins, minerals, carbohydrate, and fat.

6. The composition of claim 5 comprising, as a percentage of total calories, about 10% to about 75% carbohydrate, about 20% to about 85% fat, and about 5% to about 70% protein.

7. The composition of claim 1 wherein the composition is an oral tablet.

8. The composition of claim 1 wherein the composition is an oral liquid.

9. An oral composition for treating individuals afflicted with diabetes or impaired glucose tolerance, comprising isoleucine, leucine, valine, cysteine, and methionine; the composition having weight ratios of isoleucine to leucine, isoleucine to valine, isoleucine to cysteine, and isoleucine to methionine independently of at least about 10:1.

10. The composition of claim 9, wherein the weight ratios of isoleucine to leucine, isoleucine to valine, isoleucine to cysteine, and isoleucine to methionine are independently at least about 100:1.

11. The composition of claim 9 having weight ratios of branched chain amino acids to sulfur containing amino acids of at least about 50:1.

12. The composition of claim 9 comprising less than about 5% by weight of phenylalanine.

13. The composition of claim 9 further comprising at least one of vitamins, minerals, carbohydrate, and fat.

14. The composition of claim 13 comprising, as a percentage of total calories, about 10% to about 75% carbohydrate, about 20% to about 85% fat, and about 5% to about 70% protein.

15. The composition of claim 9 wherein the composition is an oral tablet.

16. The composition of claim 9 wherein the composition is an oral liquid.

17. An oral composition for treating individuals afflicted with diabetes or impaired glucose tolerance, comprising:
    about 10 to about 200 mg/kg of body weight of isoleucine;
    about 0.01 to about 10 mg/kg of body weight of leucine;
    about 0.01 to about 10 mg/kg of body weight of valine;
    about 0.01 to about 10 mg/kg of body weight of cysteine; and
    about 0.01 to about 10 mg/kg of body weight of methionine,
    wherein weight ratios of isoleucine to leucine, isoleucine to valine, isoleucine to cysteine, and isoleucine to methionine are independently at least about 10:1.

18. The composition of claim 17, wherein weight ratios of at least one of isoleucine to leucine, isoleucine to valine, isoleucine to cysteine, and isoleucine to methionine is at least about 100:1.

19. The composition of claim 17 comprising less than about 10 mg/kg of body weight of phenylalanine.

20. The composition of claim 17 further comprising at least one of vitamins, minerals, carbohydrate, and fat.

21. The composition of claim 17 comprising, as a percentage of total calories, about 10% to about 75% carbohydrate, about 20% to about 85% fat, and about 5% to about 70% protein.

22. The composition of claim 17 wherein the composition is an oral tablet.

23. The composition of claim 17 wherein the composition is an oral liquid.

* * * * *